(12) United States Patent
Benner

(10) Patent No.: US 8,946,397 B1
(45) Date of Patent: Feb. 3, 2015

(54) TAGGED NUCLEOSIDES THAT LEAVE NO SCAR UPON CLEAVAGE

(76) Inventor: Steven A. Benner, Gainsville, FL (US)

( * ) Notice: Subject to any disclaimer, the term of this patent is extended or adjusted under 35 U.S.C. 154(b) by 296 days.

(21) Appl. No.: 13/439,179

(22) Filed: Apr. 4, 2012

Related U.S. Application Data

(60) Provisional application No. 61/471,416, filed on Apr. 4, 2011.

(51) Int. Cl.
*C07H 21/02* (2006.01)
*C07H 19/20* (2006.01)
*C07H 7/06* (2006.01)

(52) U.S. Cl.
USPC ............. 536/23.1; 536/26.26; 536/29.2

(58) Field of Classification Search
CPC ........... C07H 19/06; C07H 21/00; C07H 1/00
See application file for complete search history.

(56) References Cited

U.S. PATENT DOCUMENTS 6,174,998 B1   1/2001   Muhlegger
7,544,794 B1   6/2009   Benner

*Primary Examiner* — Lawrence E Crane

(57) ABSTRACT

This invention provides compounds that are of the class of nucleoside analogs, and more specifically nucleoside analogs that have a non-standard nucleobase, and more specifically analogs where a side chain is appended to said non-standard nucleobase, where said side chain can be cleaved so as to leave behind no more than five atoms appended to the nucleobase as a "scar". The claimed compounds are useful as intermediates in processes that transiently introduce tags, labels, fluorescent molecules, or other species into oligonucleotides, as in sequencing using cyclic reversible termination, in in vitro selection using functionalized nucleotides that must later be PCR amplified, or in nucleotide capture protocols used in diagnostics.

2 Claims, 9 Drawing Sheets

SEQUENCE LISTING

<160> NUMBER OF SEQ ID NOS: 2

<210> SEQ ID NO 1
<211> LENGTH: 24
<212> TYPE: DNA

```
<213> ORGANISM: Artificial Sequence
<220> FEATURE:
<223> OTHER INFORMATION: Synthetic

<400> SEQUENCE: 1
gcgtaatacg actcactatg gacg                                      24

<210> SEQ ID NO 2
<211> LENGTH: 36
<212> TYPE: DNA
<213> ORGANISM: Artificial Sequence
<220> FEATURE:
<223> OTHER INFORMATION: Synthetic

<400> SEQUENCE: 2
gtcttcgtgt aacgrccata gtgagtcgta ttacgc                         36
```

TAGGED NUCLEOSIDES THAT LEAVE NO SCAR UPON CLEAVAGE

STATEMENT REGARDING FEDERALLY SPONSORED RESEARCH OR DEVELOPMENT

Figure 1:
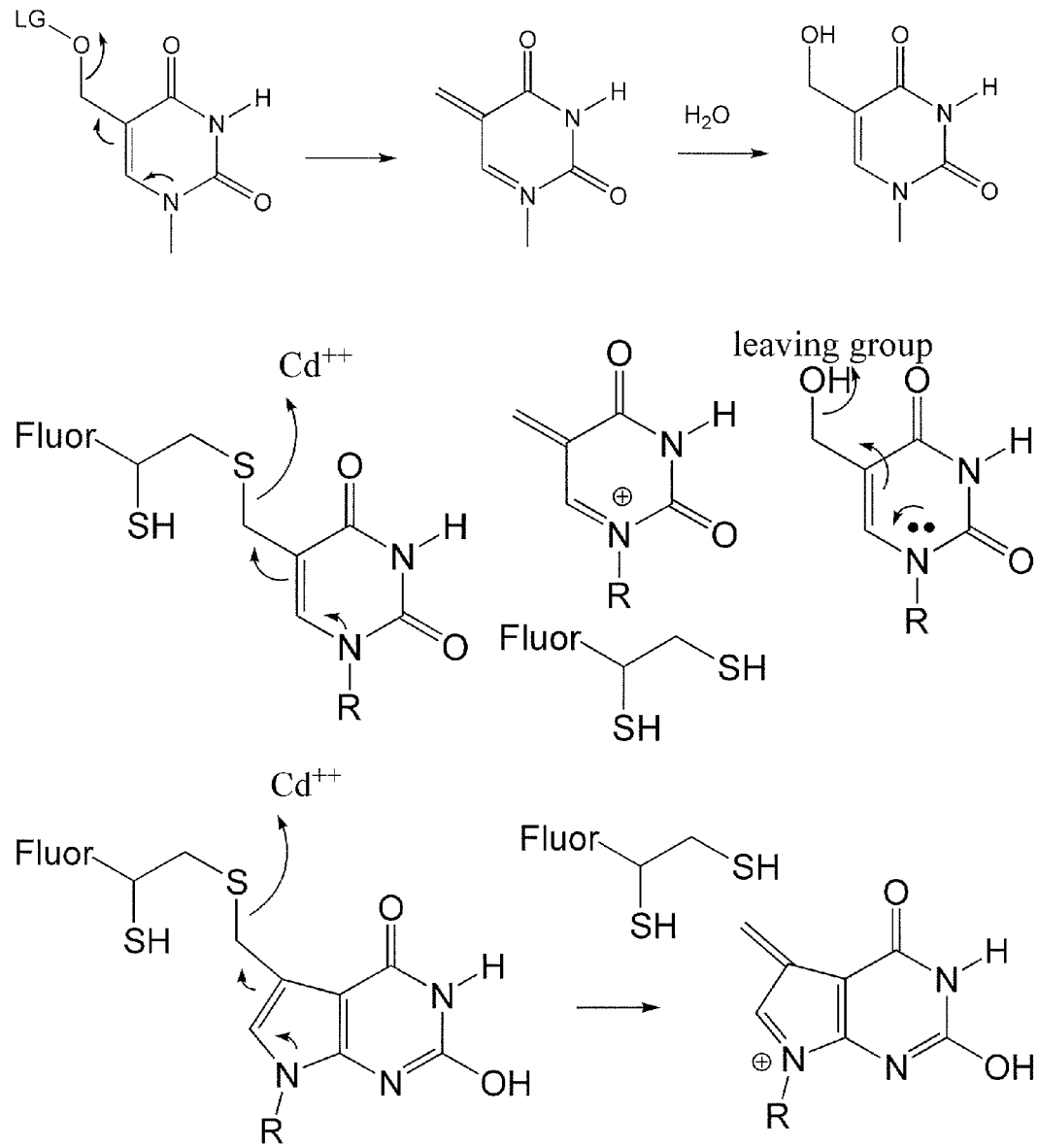

This invention was made with government support under HDTRA1-08-1-0052 awarded by DTRA and under R42HG004589-02 awarded by NHGRI. The government has certain rights in the invention.

CROSS REFERENCE TO RELATED APPLICATIONS

This application claims priority to provisional patent application 61471416

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION (1) Field of the Invention

This invention relates to nucleic acids, more specifically to nucleic acids, also known as oligonucleotides, that contain nucleotides that carry on a plurality (two or more) of their nucleobases side chains, also known as linkers and/or tags, that can be removed by simple chemical reactions that otherwise leave the oligonucleotide intact, wherein the nucleobases derived from these chemical reactions carry a residual side chain, or "scar", that is no larger than a hydroxymethyl group.

(2) Description of Related Art

Many applications involve the incorporation of tagged nucleotides into an oligonucleotide strand. For example, Ward showed nearly three decades ago that many DNA polymerases accept pyrimidine nucleoside triphosphates where a biotin tag is appended to the pyrimidine heterocycle at the 5-position. Nearly all of capillary electrophoresis-based sequencing involves the attachment of a fluorescent tag via a linker to this position in pyrimidines, or to the "seven" position of 7-deazapurines.

For many applications, it is desirable to remove the tag after it is incorporated and observed. Prominent among these are "next generation" DNA sequencing architectures that involve cyclic reversible termination [Metzker 2005]. Here, a fluorescently tagged nucleoside triphosphate carry a 3'-O-blocking group is presented to a polymerase, primer, and template. This allows the incorporation of a single fluorescently tagged nucleotide, whose fluorescence indicates which of the four standard nucleotides have been incorporated. Further sequencing requires, however, that the fluor be removed, and a variety of chemical processes have been proposed that do this. [Ruparel et al, 2005] [Ju et al, 2006] [Guo et al, 2008]. These are coupled with a variety of 31-0 blocking groups, including the 3'-$ONH_2$ group shown in certain figures herein. See also [Benner 2009], which is incorporated in its entirety herein by citation [Tasara et al, 2003].

Other applications that require removal of a tag involve addition of tagged nucleotides to a single stranded DNA molecule through the action of terminal transferase. Subsequent cloning of the product may require removal of the tag. Likewise, oligonucleotides that have very high density of labeling need to have the labels removed prior to cloning or other downstream analysis.

One serious problem in architectures that remove the tag is that the removal process leaves behind a "scar", a fragment of the linker that carried the tag. In cyclic reversible termination architectures, this scar is on the 3'-terminal nucleotide of an oligonucleotide that is the primer in the next cycle of primer extension. Extensive studies with polymerases have shown that the presence of a scar on the 3'-nucleotide of a primer hinders, with many polymerases, the addition of a tagged nucleotide in that cycle. This means that many architectures that use cyclic reversible termination cannot fully tag the species.

Together, the community has long known that it would be desirable to have nucleoside triphosphates that carry a tag where the tag can be removed by a reaction process that leaves behind only a small scar or, more preferably, no scar at all. A small scar is a 5-position methyl group or a 5-position hydroxymethyl group. Both occur frequently in nucleic acids, most obviously on thymine (which has a methyl group in standard DNA) and in modified nucleic acids (as in hydroxymethylcytosine). No scar means that a hydrogen ends up in place of a tag. In this discussion, both cases are called "scarless".

Those seeking to obtain scarless products have focused on linkers that acylate or alkylate an exocyclic amino group of a nucleobase at this position. These require either harsh chemical conditions or harsh photochemical conditions to remove. For example, Metzker recently proposed to tag nucleobases using photochemically removable side chains [Wu et al, 2007]. Subsequently, Siddiqi proposed tags attached to the nucleobases for the purpose of sequencing single nucleic acid molecules, in the hope of avoiding amplification bias [Siddiqi 2008].

BRIEF SUMMARY OF THE INVENTION

The purpose of this invention is to provide a series of linking groups attached to nucleoside analogs that, when subjected to chemical treatment, leave behind either no scar or a small scar. This is done in one of two architectures. The first has the nucleobase push electrons, causing the preponderance of the linker to leave, where an added reagent assists that leaving. The second architecture employs a reagent that transforms a functional group in the linker to permit it to push electrons, having the nucleobase leave.

BRIEF DESCRIPTION OF THE SEVERAL VIEWS OF THE DRAWING(S)

FIG. 1. The structure and reactivity of nucleoside precursors tagged with linkers that leave, after cleavage, a hydroxymethyl scar, via a reaction that involves a "push" of electrons from the nucleobase analog.

Figure 2:
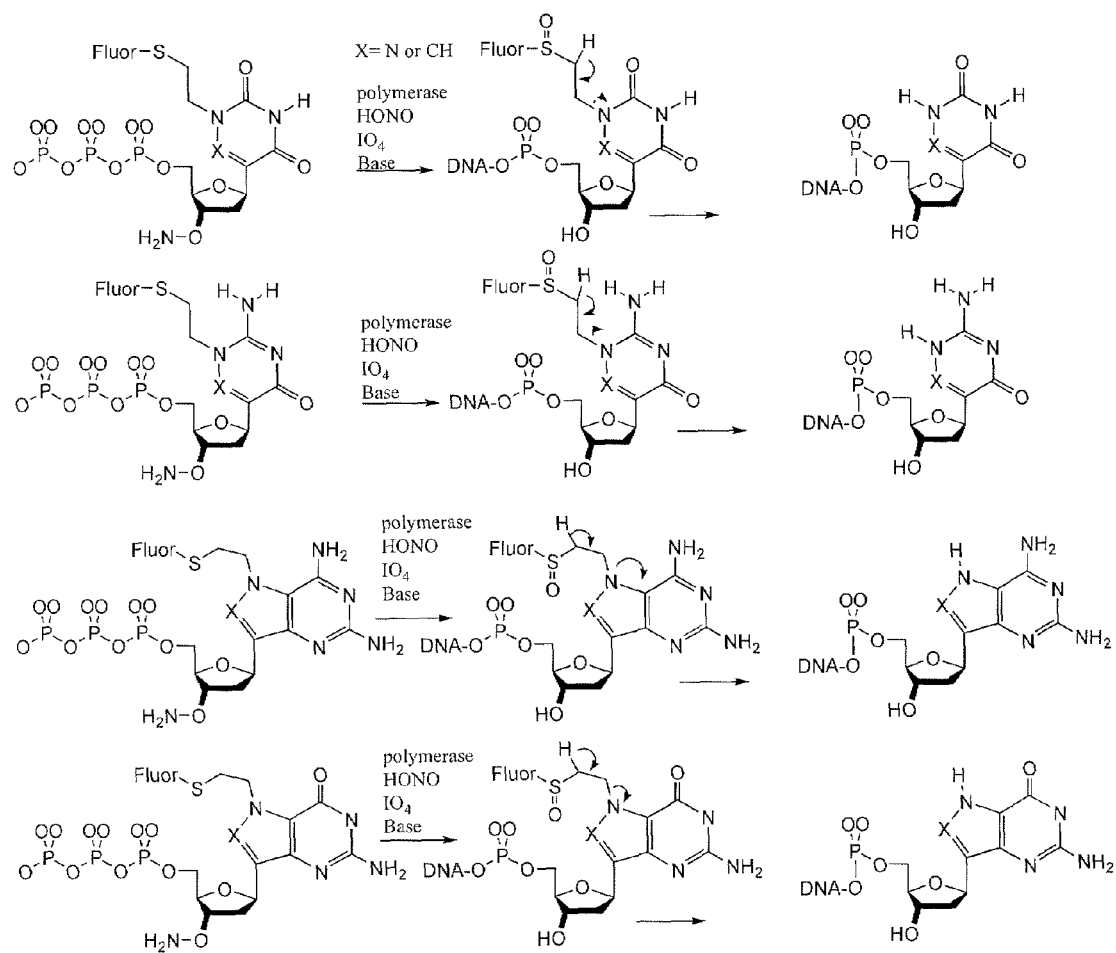

FIG. 2. The structure and reactivity of nucleoside precursors tagged with linkers that, upon cleavage, generate a linker that pushes electrons toward the nucleobase, which then departs as a leaving group, where a sulfoxide or sulfone in the linker enolizes and thereby provides the electron "push".

Figure 3:
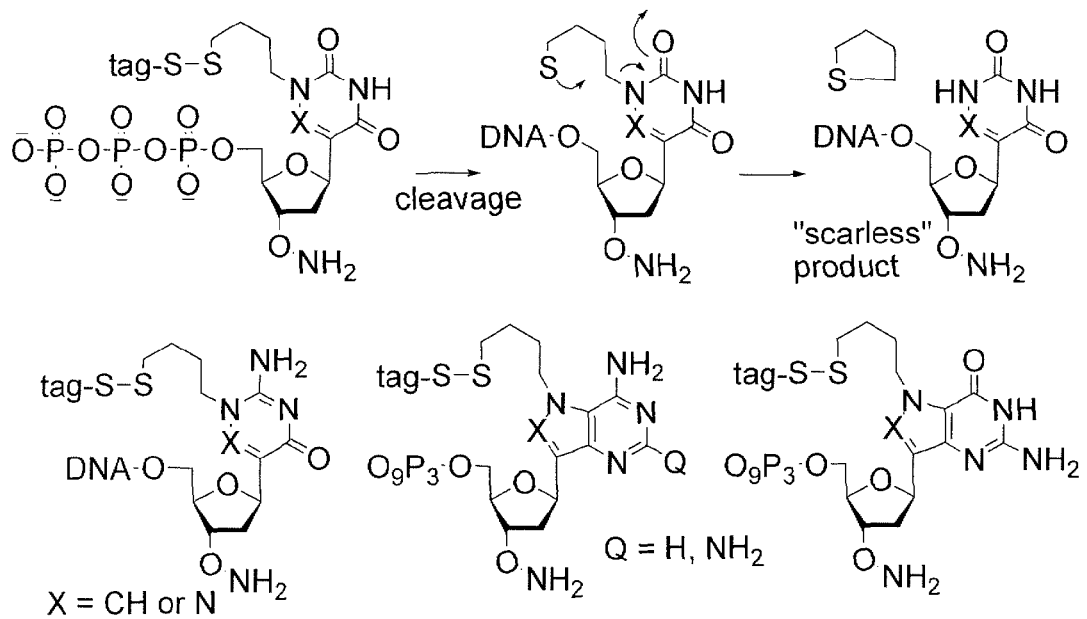

FIG. 3. The structure and reactivity of nucleoside precursors tagged with linkers that, upon cleavage, generate a linker that leaves behind no scar via an SN2 reaction.

Figure 5:
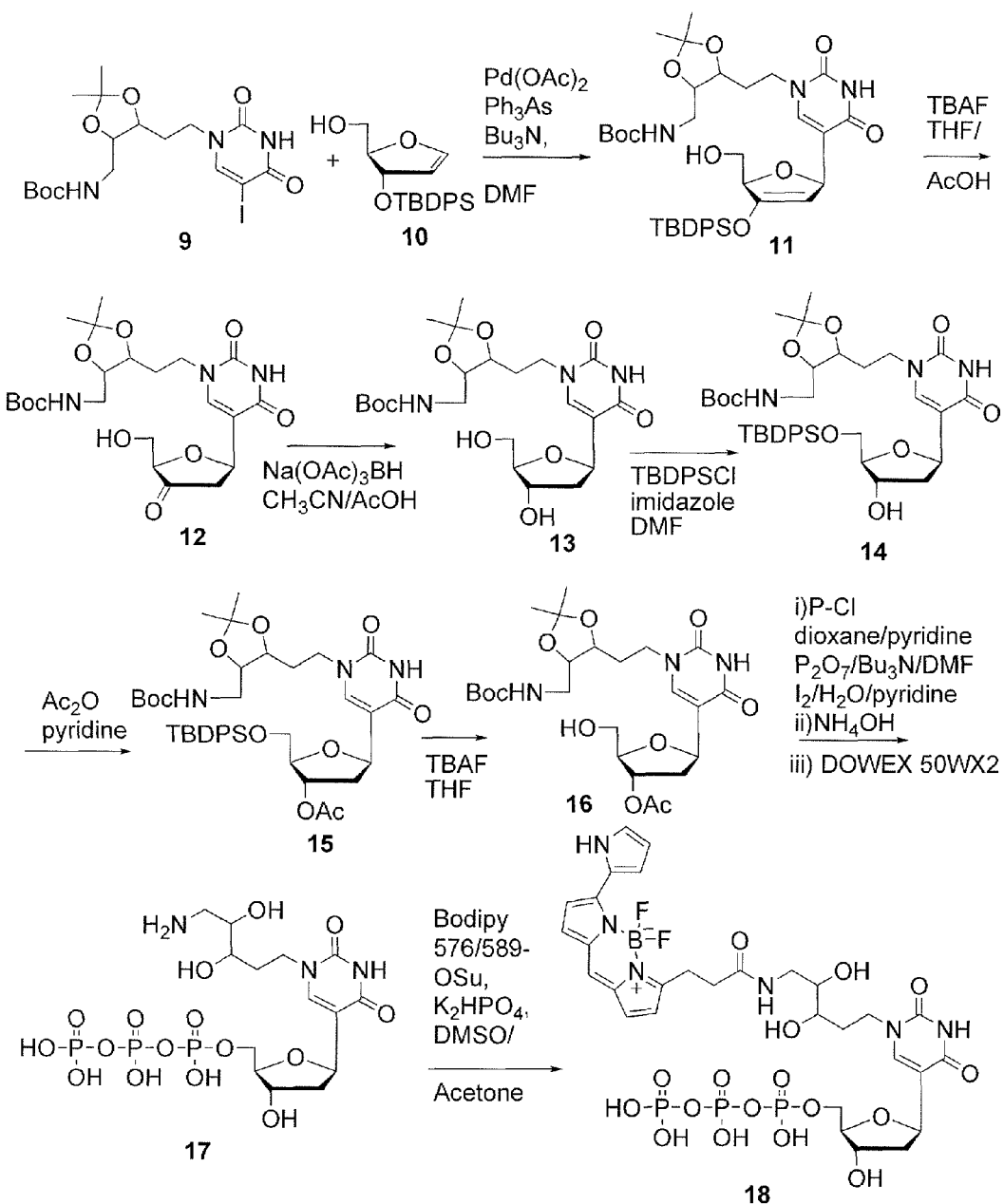

FIG. 5. Scheme for preparing the linker and the uridine analog for the "linker push" architecture of tags that leaves behind scarless products.

Figure 6:
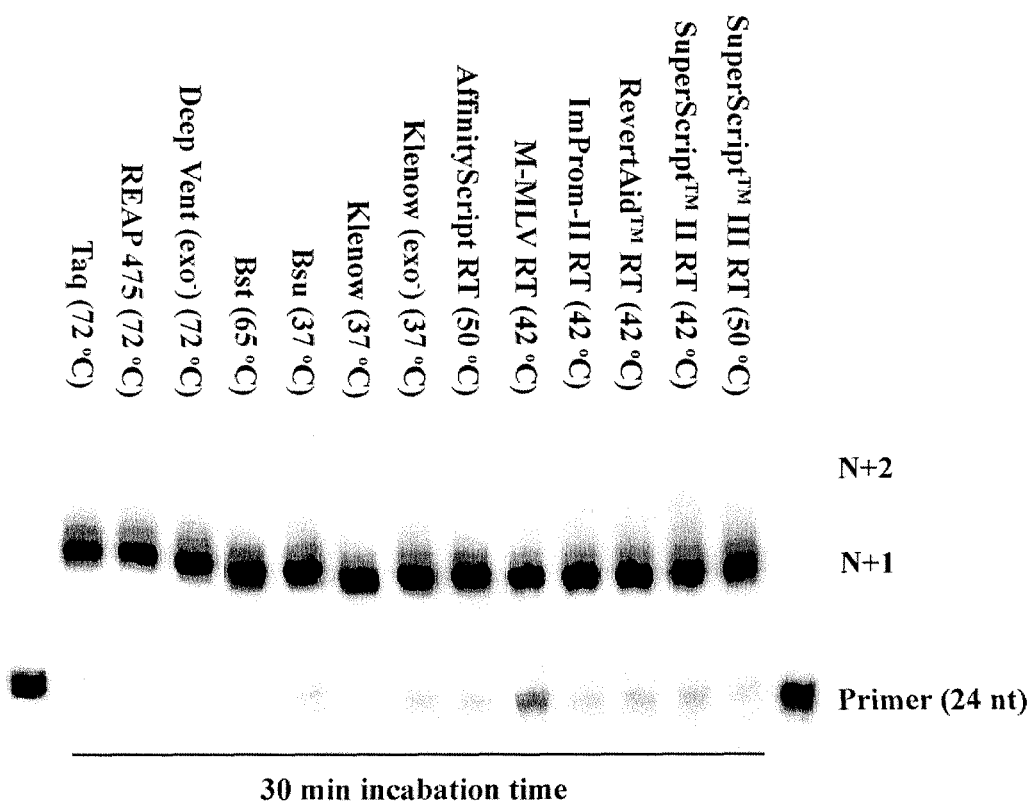

FIG. 6. Polymerase incorporation of compound 18.

Figure 7:
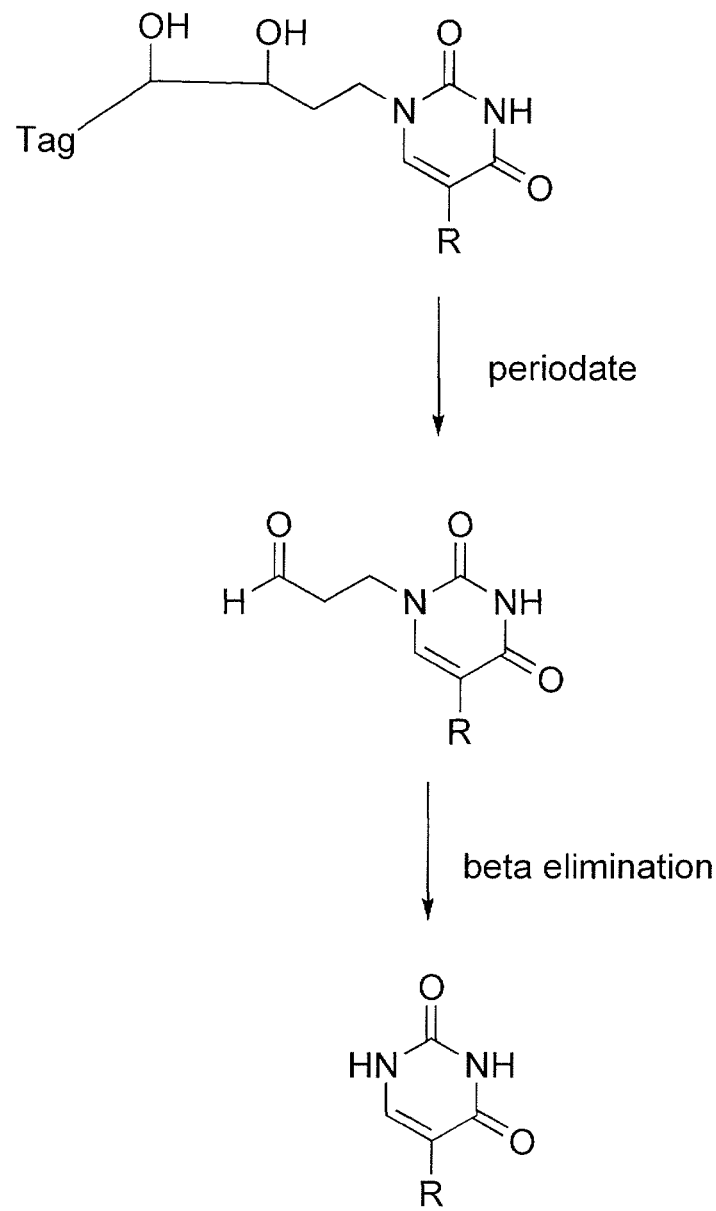

FIG. 7. Demonstration that a scarless product can be generated using nucleotides of the instant invention.

Figure 8:
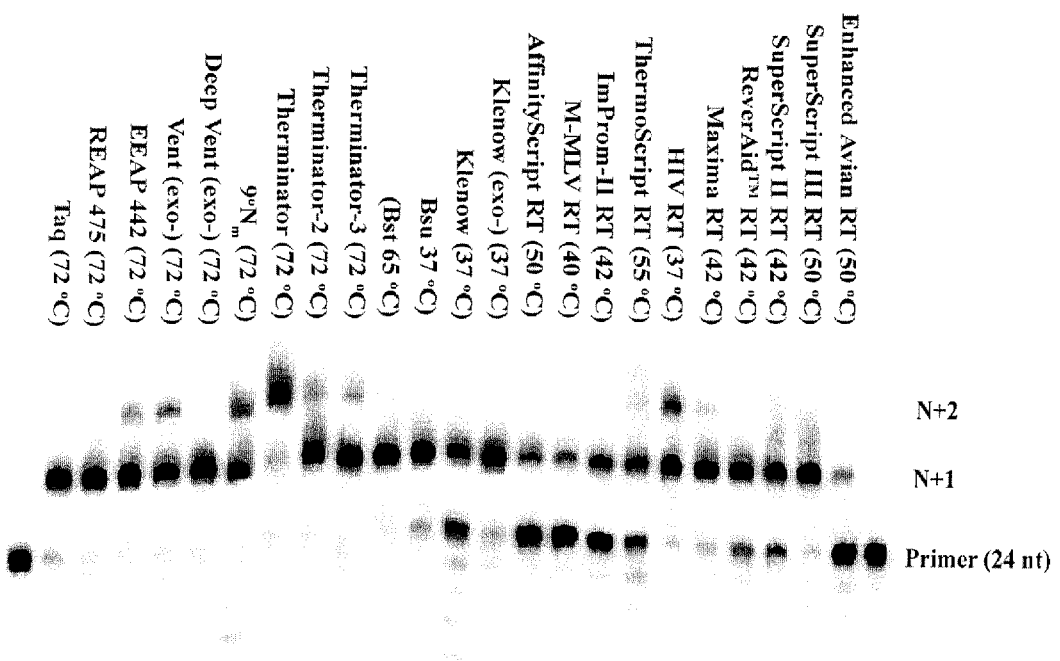

FIG. 8. Extension of a primer on a template that calls for the addition of two consecutive T analogs (in fact, 2'-deoxypseudouridine having on the heterocyclic N a $(CH_2)_2$—(CHOH)—(CHOH)—$CH_2$—NH—$(CO)(CH_2)_2$-Bodipy unit, as in FIG. 6) stops with certain of the indicated polymerases after the addition of one T analog, even without a 3'-$ONH_2$ group. Subsequent removal of the side chain allows primer extension to continue. These results suggest that these triphosphates will support sequencing during synthesis without the need for attaching a 3'-blocking group! Incubation is for 2 min with the template primer combination.

SEQ ID NO 1
5'-GCG TAA TAC GAC TCA CTA TGG ACG

SEQ ID NO 2
3'-CGC ATT ATG CTG AGT GAT ACC TGC AAT GTG CTT CTG

Figure 9:
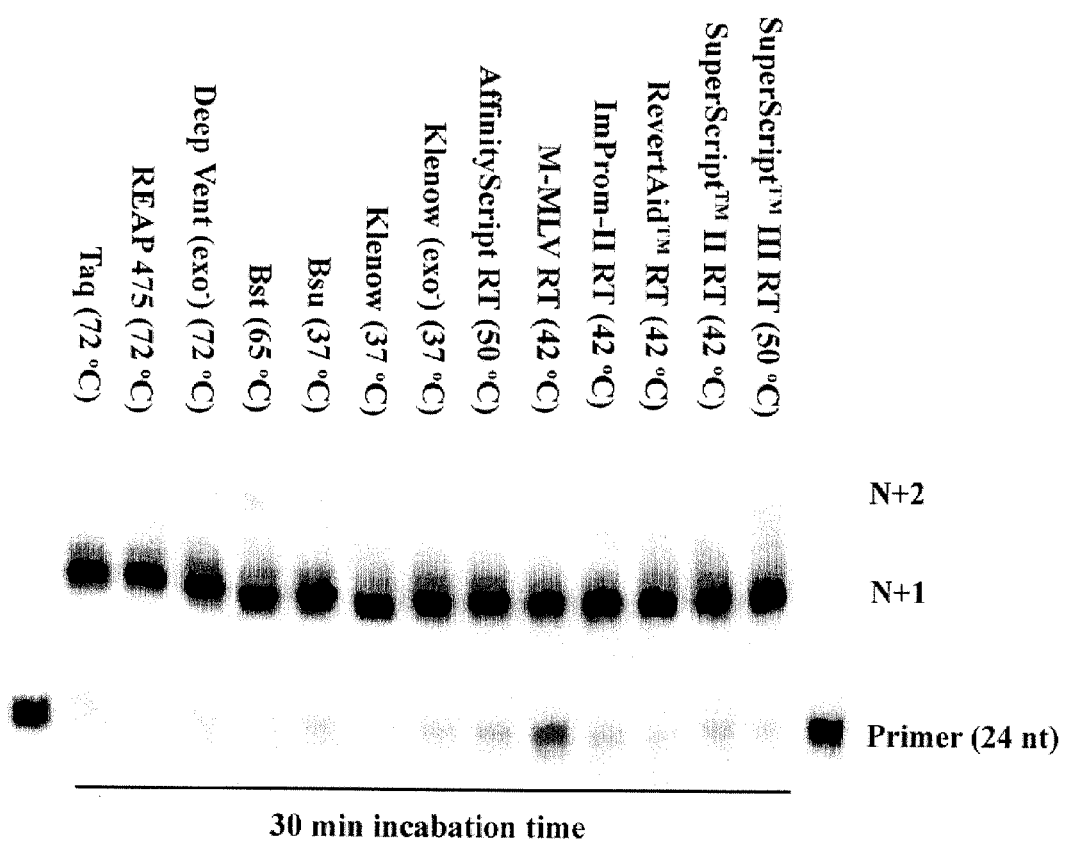

FIG. 9. As in FIG. 8, but with 30 min incubation.

DETAILED DESCRIPTION OF THE INVENTION

Two architectures are disclosed here for creating nucleotides that, once incorporated into an oligonucleotide, can be cleaved without leaving a scar. The first architecture, illustrated in FIG. 1, involves a "push" from the nucleobase to force a leaving group in the linker to depart, where the ability of the linker to depart is enhanced by added reagents that enhance the ability of a fragment of the linker to act as a leaving group. Following its departure, water from solvent adds back to the product to create a hydroxymethyl group replacing the linker. This is implemented with either standard pyrimidines or 9-deazapurines.

The second architecture involves a "push" from the linker after it is transformed by a chemical reaction. Illustrated in FIG. 2 with thioether linkages and, in its presently preferred form, in FIG. 3 with a 1,2-diol in the linker, this second class has the nucleobase itself be a leaving group. While not wishing to be bound by theory, the inventive step is to recognize that a C-glycoside can allow the linkage to be attached to a nitrogen whose conjugate acid form has a pKa in a range from approximately 8 to approximately 10.

The pKa's of several of the nucleobase analogs that implement this invention is found in the literature. For example, Luyten et al. summarized the literature (see references therein) and reported new pKa's for formycin A (9.6, for deprotonation of N7), formycin B (10.4 for the deprotonation of N7), pseudoisocytidine (9.0 for the deprotonation of N3) and pseudouridine (9.1, cite of deprotonation unclear) [Luyten et al, 1997]. Adding another nitrogen to a ring (e.g., proceeding from 9-deazapurines to 8-aza-9-deazapurines or from pseudouridine to 6-azpseudouridine or, correctly numbered, 4-azpseudouridine) lowers the relevant pKa by 1-2 pKa units.

Showing that this inventive concept was reducible to practice, 1,2-diol linkers were prepared for pseudouracil, an analog of the nucleobase in natural thymidine. Cleavage of the 1,2-diol with periodate generated an aldehyde, which readily fragmented at modest pH to give pseudouracil derivatives with a half life of just minutes.

The structure of the linker past the cleavable functionality is incidental to the invention. Thus, that linker can carry any kind of tag, including a fluorescent tag, a redox active tag, and a mass spectral tag. Further, the linker can be an aminoalkyl group (as in Example 1), a carboxyalkyl group, a thioalkyl group, or a hydroxyalkyl group.

This disclosure teaches that an additional nitrogen can be incorporated at either position 6 in the pyrimidines (using analogous numbering to the standard nucleobases) or at position 8 in the purines (using analogous numbering to the standard nucleobases). This additional nitrogen has the effect of making the beta elimination process faster, at the cost of making the product more "unnatural".

The nucleoside analogs with the tags and the nucleobases appropriately protected and the 2'-OH group acetylated, as in the standard Ludwig-Eckstein procedure, can be converted into triphosphates using that procedure [Ludwig et al, 1989].

An additional unexpected discovery was then made when testing polymerases with triphosphates of C-glycosides, 2'-deoxypseudouridine in particular, with side chains that would generate an aldehyde unit that could fragment, as shown in FIG. 7, to give a "thymine". Here, polymerases were found that did not need a 3'-$ONH_2$ unit to stop extension after a single nucleotide incorporation. This is analogous to the Metzker approach mentioned in the introduction of using a base modification, rather than a 3'-block to achieve reversible termination. However, unlike the Metzker modifications, the modifications disclosed here are attached to what would be formally the 5-position (by analogy to the numbering system used in standard nucleotides). Further, they are removable by a chemical step, not a photochemical step.

EXAMPLES

Example 1

Synthesis of a Representative T Analog

Figure 4:
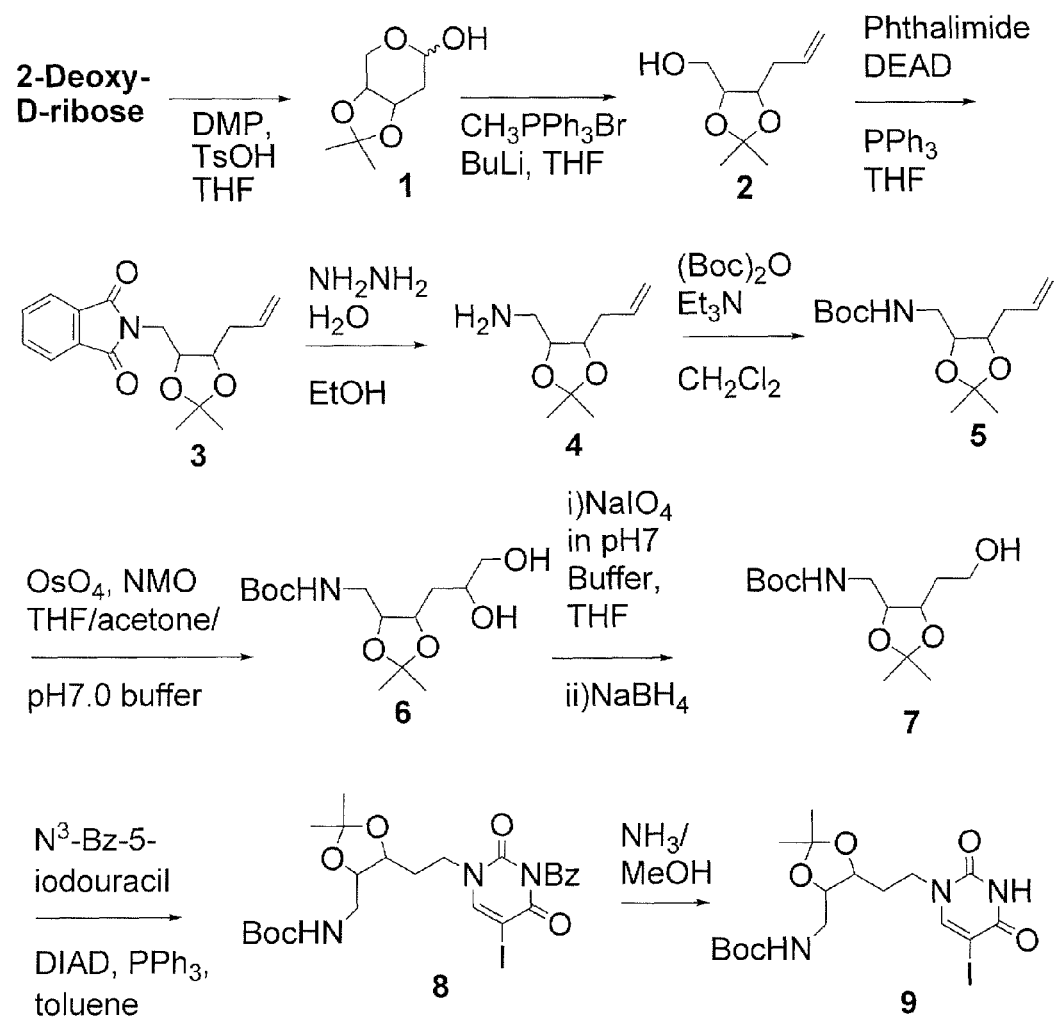

2-Deoxy-3,4-O-isopropylidene-D-erythro-pentopyronose (1) FIGS. 4 and 5

To a stirred suspension of 2-deoxy-D-ribose (5 g, 37.3 mmol) in THF (100 mL) were added p-toluenesulfonic acid (150 mg, 0.79 mmol) and 2,2-dimethoxypropane (10 mL) at room temperature. The mixture was stirred at room temperature for 45 min, neutralized with $Et_3N$ and concentrated. The residue was diluted with EtOAc and extracted with $H_2O$. The organic layer was dried ($Na_2SO_4$), filtered and concentrated. The residue was resolved by silica gel column chromatography (Hex/EtOAc=1/2) to give compound 1 (4.26 g, 24.5 mmol, 66%) as an oil.

$^1$H NMR (CDCl$_3$, 300 MHz) δ 5.21 (m, 1H), 4.44 (m, 1H), 4.13 (m, 1H), 3.91 (m, 1H), 3.65 (m, 1H), 3/23 (m, 1H), 2.19-2.27 (m, 1H), 1.72-1.91 (m, 1H), 1.49, 1.33 (2s, 6H).

(5-Allyl-2,2-dimethyl-1,3-dioxolan-4-yl)methanol (2)

To a stirred suspension of methyltriphenylphosphonium bromide (24.86 g, 69.6 mmol) in THF (180 mL) was added 2.5M solution of BuLi in hexane (27.8 mL, 69.5 mmol) at This mixture was stirred at room temperature for 1 h and cooled to 0° C. A solution of compound 1 (4.04 g, 23.2 mmol) in THF (30 mL) was added to this mixture at 0° C. The reaction mixture was stirred at room temperature for 2 h and aq. ammonium chloride solution (100 mL) was added. The mixture was extracted with EtOAc. The organic layer was washed with brine, dried (Na$_2$SO$_4$), filtered and concentrated. The residue was resolved by silica gel column chromatography (Hex/EtOAc=1/1) to give compound 2 (3.1 g, 18 mmol, 78%) as an oil.

$^1$H NMR (CDCl$_3$, 300 MHz) δ 5.76-5.89 (m, 1H), 5.07-5.17 (m, 2H), 4/14-4/28 (m, 2H), 3.61-3.65 (m, 2H), 2.22-2.44 (m, 2H), 2.05 (t, 1H, J=6.0), 1.47, 1.36 (2s, 6H); $^{13}$C NMR (CDCl$_3$, 75 MHz) δ 134.4, 116.6, 108.5, 78.0, 76.5, 61.8, 33.9, 28.4, 25.7.

2-((5-allyl-2,2,-dimethyl-1,3-dioxolan-4-yl)methyl) isoindoline-1,3-dione (3)

To a stirred solution of compound 2 (2.8 g, 16.3 mmol) in THF (120 mL) were added PPh$_3$ (6.4 g, 24.4 mmol) and DEAD (40% in toluene, 10.6 mL, 24.3 mmol) at 0° C. After 20 min stirring, phthalimide (3.59 g, 24.4 mmol). The reaction mixture was stirred overnight at room temperature, concentrated, diluted with EtOAc (300 mL) and extracted with aq. NaHCO$_3$ solution (100 mL). The organic layer was dried (Na$_2$SO$_4$), filtered and concentrated. The residue was purified by silica gel column chromatography (Hex/EtOAc=2/1) to give compound 3 (4.74 g, 15.7 mmol, 97%) as an oil. $^1$H NMR (CDCl$_3$, 300 MHz) δ 7.80-7.85 (m, 2H), 7.68-7.73 (m, 2H), 5.82 (m, 1H), 5.13-5.24 (m, 2H), 4.48 (m, 1H), 4.26 (m, 1H), 3.90 (dd, 1H, J=10.5, 13.5), 3.52 (dd, 1H, J=3.0, 13.5), 2.37-2.57 (m, 2H), 1.53, 1.30 (2s, 6H); $^{13}$C NMR (CDCl$_3$, 75 MHz) δ 168.5, 134.1, 133.9, 132.4, 123.5, 118.0, 109.1, 76.5, 74.3, 39.1, 33.5, 28.2, 26.1.

tert-Butyl ((5-allyl-2,2,-dimethyl-1,3-dioxolan-4-yl) methyl)carbamate (5)

To a stirred solution of compound 3 (4.74 g, 15.7 mmol) in EtOH (120 mL) was added hydrazine hydrate (3 mL) at room temperature. The reaction mixture was stirred at 60° C. for 3 h, cooled to rt and filtered (washed with CH$_2$Cl$_2$). The filtrate was concentrated to give crude compound 4, which was dissolved in CH$_2$Cl$_2$ (80 mL). To this solution were added Et$_3$N (4.38 mL, 31.4 mmol) and (Boc)$_2$O (3.44 g, 15.8 mmol) at room temperature. The reaction mixture was stirred at room temperature for 3 h, poured into sat. NaHCO$_3$ sol'n and extracted with CH$_2$Cl$_2$. The organic layer was dried (Na$_2$SO$_4$), filtered and concentrated. The residue was resolved by silica gel column chromatography (Hex/EtOAc=4/1 to 3/1) to give compound 5 (2.75 g, 10.1 mmol, 64%) as an oil.

$^1$H NMR (CDCl$_3$, 300 MHz) δ 5.75 (m, 1H), 5.08-5.18 (m, 2H), 4.85 (m, 1H), 4.17 (m, 1H), 4.09 (m, 1H), 3.41 (m, 1H), 2.93 (m, 1H), 2.20-2.40 (m, 2H), 1.45 (s, 3H), 1.43 (s, 9H), 1.33 (s, 3H); $^{13}$C NMR (CDCl$_3$, 75 MHz) δ 156.1, 134.1, 117.8, 108.5, 79.7, 76.6, 41.1, 33.8, 28.6, 28.5, 25.9.

tert-Butyl ((5-(2-hydroxyethyl)-2,2,-dimethyl-1,3-dioxolan-4-yl)methyl)carbamate (7)

Compound 5 (2.75 g, 10.1 mmol) was dissolved in 1/1/1 mixture of THF, acetone and aq. pH 7.0 buffer (45 mL) at room temperature. NMO (1.56 g, 13.3 mmol) was added followed by OsO$_4$ (2.5% in t-butanol, 12.5 mL) at rt. The reaction mixture was stirred overnight at room temperature, and sodium bisulfite (10.13 g) in water (150 mL) was added. The mixture was stirred for 10 min and extracted with EtOAc (×2). The combined organic layers were dried (Na$_2$SO$_4$), filtered and concentrated to give crude compound 6.

Compound 6 was dissolved in THF (80 mL) and a solution of NaIO$_4$ (4.28 g, 20 mmol) in aq. pH 7.0 buffer (60 mL) was added at rt. After 1.5 h stirring, NaBH$_4$ (1 g, 26.4 mmol) at room temperature. The reaction mixture was stirred at room temperature for 1 h and partitioned between EtOAc and brine. The organic layer was dried (Na$_2$SO$_4$), filtered and concentrated. The residue was resolved by silica gel column chromatography (Hex/EtOAc=3/7) to give compound 7 (2.29 g, 8.38 mmol, 83%) as an oil.

$^1$H NMR (CDCl$_3$, 300 MHz) δ 4.90 (m, 1H), 4.28 (m, 1H), 4.11 (m, 1H), 3.73-3.84 (m, 2H), 3.38 (m, 1H), 2.92 (m, 1H), 2.42 (dd, 1H, J=4.2, 6.6), 1.63-1.80 (m, 2H), 1.44 (s, 3H), 1.42 (s, 9H), 1.33 (s, 3H); $^{13}$C NMR (CDCl$_3$, 75 MHz) δ 156.2, 108.7, 79.8, 77.0, 76.1, 61.1, 41.3, 31.7, 28.6, 28.5, 25.9.

N$^3$-Benzoyl-1-(tert-Butyl((5-ethyl-2,2,-dimethyl-1,3-dioxolan-4-yl)methyl)carbamate)-5-iodouracil (8)

To a stirred solution of compound 7 (1.77 g, 6.5 mmol) in THF (60 mL) was added N$^3$-Bz-5-iodouracil (2.43 g, 7.1 mmol). After 10 min, PPh$_3$ (1.86 g, 7.1 mmol) was added. After 10 min, DEAD (40% in toluene, 3.1 mL, 7.1 mmol) was added. The mixture was stirred at room temperature for 3 h and concentrated. The residue was resolved by silica gel column chromatography (Hex/EtOAc=1/1) to give compound 8 (2.7 g, 4.5 mmol, 70%) as a foam.

$^1$H NMR (CDCl$_3$, 300 MHz) δ 7.88-7.91 (m, 2H), 7.78 (s, 1H), 7.63 (m, 1H), 7.47 (t, 2H, J=7.8), 4.82 (m, 1H), 4.00-4.16 (m, 3H), 3.79 (m, 1H), 3.35 (m, 1H), 2.93 (m, 1H), 1.82-1.95 (m, 2H), 1.46 (s, 3H), 1.42 (s, 9H), 1.34 (s, 3H); $^{13}$C NMR (CDCl$_3$, 75 MHz) δ 168.0, 159.6, 156.0, 149.7, 149.5, 135.5, 131.2, 130.8, 129.5, 109.1, 79.9, 76.7, 74.1, 67.1, 47.8, 41.1, 28.6, 28.5, 28.3, 25.8.

1-(tert-Butyl((5-ethyl-2,2,-dimethyl-1,3-dioxolan-4-yl)methyl)carbamate)-5-iodouracil (9)

A solution of compound 8 (1.37 g, 2.29 mmol) in 7N NH$_3$ in MeOH (40 mL) was stirred overnight at room temperature and concentrated. The residue was resolved by silica gel column chromatography (Hex/EtOAc=1/2) to give compound 9 (800 mg, 1.62 mmol, 71%) as a white foam.

$^1$H NMR (CDCl$_3$, 300 MHz) δ 9.22 (brs, 1H), 7.69 (s, 1H), 4.88 (m, 1H), 3.99-4.18 (m, 3H), 3.73 (m, 1H), 3.38 (m, 1H), 2.93 (m, 1H), 1.91 (m, 1H), 1.74 (m, 1H), 1.44 (s, 3H), 1.43 (s, 9H), 1.334 (s, 3H); $^{13}$C NMR (CDCl$_3$, 75 MHz) δ 160.8, 156.1, 150.6, 149.8, 109.0, 80.0, 76.7, 73.8, 67.5, 47.3, 41.2, 28.6, 28.1, 25.8.

1-(tert-Butyl((5-ethyl-2,2,-dimethyl-1,3-dioxolan-4-yl)methyl)carbamate)-5-(2',5'-dihydro-4'-t-butyl-diphenylsilyloxy-5'-hydroxymethyl-2'-furanyl)-2,4 (1H,3H)-pyrimidinone (11)

A mixture of Pd(OAc)$_2$ (190 mg, 0.85 mmol) and AsPh$_3$ (519 mg, 1.69 mmol) in DMF (45 mL) was stirred at room temperature for 30 min. To this mixture was added a solution of glycal 10 (2.4 g, 6.77 mmol), compound 9 (2.8 g, 5.65 mmol) and Bu$_3$N (2.67 mL, 11.3 mmol) in DMF (30 mL). The reaction mixture was stirred at 60° C. for 18 h, cooled to room temperature and concentrated. The residue was resolved by silica gel column chromatography (Hex/EtOAc=3/7) to give compound 11 (1.9 g, 2.64 mmol, 47%) as a yellow foam.

$^1$H NMR (CDCl$_3$, 300 MHz) δ 7.80 (m, 2H), 7.71 (m, 2H), 7.39-7.47 (m, 7H), 7/09 (brs, 1H), 5.53 (m, 1H), 4.91 (m, 1H), 4.69 (m, 1H), 4.08-4.20 (m, 3H), 3.80-3.93 (m, 2H), 3.73 (m, 2H), 2.98-3.42 (m, 3H), 1.79 (m, 2H), 1.42 (s, 9H), 1.40 (s, 3H), 1.28 (s, 3H), 1.05 (s, 9H).

1-(tert-Butyl((5-ethyl-2,2,-dimethyl-1,3-dioxolan-4-yl)methyl)carbamate)-2'-deoxy-pseudouridine (13)

To a stirred solution of compound 11 (1.9 g, 2.64 mmol) in THF (25 mL) were added AcOH (0.75 mL) and 1M TBAF in THF (3.95 mL, 3.95 mmol) at 0° C. After being stirred at 0° C. for 1 h, the reaction mixture was concentrated to give crude compound 12. Compound 12 was dissolved in $CH_3CN$/AcOH (2/1, 30 mL) and $Na(OAc)_3BH$ (838 mg, 3.95 mmol) was added at 0° C. The reaction mixture was stirred at 0° C. for 1 h and acetone (5 mL) was added. After the solvent was removed, the residue was resolved by silica gel column chromatography ($CH_2Cl_2$/MeOH=10/1 to 7/1) to give compound 13 (700 mg, 1.44 mmol, 55%) as a white solid.

$^1$H NMR (DMSO-$d_6$, 300 MHz) δ 11.29 (brs, 1H), 7.55 (s, 1H), 6.82 (t, 1H, J=5.7), 4.96 (d, 1H, J=3.6), 4.75 (m, 1H), 4.69 (t, 1H, J=5.7), 3.99-4.09 (m, 3H), 3.80 (m, 1H), 3.60-3.69 (m, 2H), 3.39 (d, 2H, J=5.1), 3.14 (d, 1H, J=3.6), 3.02 (m, 1H), 2.89 (m, 1H), 1.96-2.02 (m, 1H), 1.34 (s, 9H), 1.32 (s, 3H), 1.21 (s, 3H); $^{13}$C NMR (DMSO-$d_6$, 75 MHz) δ 163.6, 158.2, 151.2, 142.4, 114.2, 108.1, 87.8, 78.5, 76.1, 74.8, 73.9, 72.8, 62.9, 41.4, 41.0, 39.4, 28.9, 26.4.

5'-O-tert-Butyldiphenylsilyl-1-(tert-butyl((5-ethyl-2,2,-dimethyl-1,3-dioxolan-4-yl)methyl)carbamate)-2'-deoxy-pseudouridine (14)

To a stirred solution of compound 13 (690 mg, 1.42 mmol) in DMF (15 mL) were added imidazole (291 mg, 4.28 mmol) and TBDPSCl (0.45 mL, 1.72 mmol) at 0° C. The reaction mixture was attired at room temperature overnight and concentrated. The residue was resolved by silica gel column chromatography (Hex/EtOAc=1/4) to give compound 14 (780 mg, 1.08 mmol, 76%) as a white foam.

$^1$H NMR (CDCl$_3$, 300 MHz) δ 9.17 (brs, 1H), 7.64-7.69 (m, 4H), 7.35-7.43 (m, 6H), 7.29 (s, 1H), 5.02 (dd, 1H, J=9.4, 9.9), 4.85 (m, 1H), 4.49 (m, 1H), 3.99-4.10 (m, 31-1), 3.66-3.84 (m, 4H), 3.34 (m, 1H), 2.90 (m, 1H), 2.43 (m, 1H), 1.68-1.89 (m, 4H), 1.42 (s, 9H), 1.35 (s, 3H), 1.23 (s, 3H), 1.04 (s, 9H); $^{13}$C NMR (CDCl$_3$, 75 MHz) δ 162.8, 156.4, 150.8, 140.7, 135.7, 135.6, 133.5, 133.3, 130.1, 125.1, 128.0, 115.5, 108.8, 86.9, 79.8, 76.7, 74.3, 64.7, 47.4, 28.6, 28.4, 27.1, 25.8, 19.5.

3'-O-Acetyl-5'-O-tert-butyldiphenylsilyl-1-(tert-butyl((5-ethyl-2,2,-dimethyl-1,3-dioxolan-4-yl)methyl)carbamate)-2'-deoxy-pseudouridine (15)

A mixture of compound 14 (770 mg, 1.07 mmol) and Ac$_2$O (0.15 mL, 1.59 mmol) in pyridine (10 mL) was stirred at room temperature overnight and concentrated. The residue was resolved by silica gel column chromatography (Hex/EtOAc=1/2) to give compound 15 (720 mg, 0.94 mmol, 88%) as a white foam.

$^1$H NMR (CDCl$_3$, 300 MHz) δ 9.16 (brs, 1H), 7.65-7.68 (m, 4H), 7.26-7.47 (m, 7H), 5.38 (m, 1H), 4.90 (dd, 1H, J=4.8, 10.8), 4.82 (m, 1H), 3.99-4.10 (m, 3H), 3.58-3.92 (m, 4H), 3.30 (m, 1H), 2.86 (m, 1H), 2.50 (m, 1H), 2.08 (s, 3H), 1.69-1.94 (m, 3H), 1.43 (s, 9H), 1.37 (s, 3H), 1.25 (s, 3H), 1.04 (s, 9H); $^{13}$C NMR (CDCl$_3$, 75 MHz) δ 170.8, 162.8, 156.0, 150.7, 149.9, 136.4, 135.7, 135.6, 133.5, 133.1, 130.2, 130.1, 128.1, 128.0, 124.0, 114.9, 108.9, 85.1, 79.8, 74.4, 73.9, 64.4, 47.5, 39.8, 28.6, 28.4, 27.0, 25.7, 21.4, 19.5.

3'-O-Acetyl-1-(tert-butyl((5-ethyl-2,2,-dimethyl-1,3-dioxolan-4-yl)methyl)carbamate)-2'-deoxy-pseudouridine (16)

To a stirred solution of compound 15 (720 mg, 0.94 mmol) in THF (10 mL) was added Et$_3$N.3HF (0.31 mL, 1.89 mmol). The reaction mixture was stirred at room temperature overnight and concentrated. The residue was resolved by silica gel column chromatography (CH$_2$Cl$_2$/MeOH=15/1 to 10/1) to give compound 16 (440 mg, 0.84 mmol, 89%) as a white solid.

$^1$H NMR (DMSO-$d_6$, 300 MHz) δ 11.37 (brs, 1H), 7.64 (s, 1H), 6.81 (t, 1H, J=5.7), 5.10 (m, 1H), 4.89 (m, 1H), 4.72 (dd, 1H, J=5.1, 10.5), 4.00-4.10 (m, 2H), 4.87 (m, 1H), 3.19-3.56 (m, 4H), 2.87-3.10 (m, 2H), 2.10 (dd, 1H, J=5.4, 13.5), 2.03 (s, 3H), 1.91-1.99 (m, 1H), 1.66-1.81 (m, 2H), 1.33 (s, 9H), 1.32 (s, 3H), 1.22 (s, 3H); $^{13}$C NMR (DMSO-$d_6$, 75 MHz) δ 170.9, 163.7, 156.3, 151.2, 143.1, 112.8, 108.1, 85.3, 78.6, 77.0, 76.1, 74.8, 62.5, 46.8, 38.6, 28.8, 28.5, 26.3, 21.6.

1-(5-amino-3,4-dihydroxypentyl)-2'-deoxy-pseudouridine-5'-triphosphate (17)

To a solution of compound 16 (430 mg, 0.82 mmol) in pyridine (3.3 mL) and dioxane (2.8 mL) was added a solution of 2-chloro-4H-1,3,2-benzodioxaphosphorin-4-one (213 mg, 1.15 mmol) in dioxane (2.1 mL) at room temperature. After 20 min a mixture of tributylammonium pyrophosphate in DMF (0.2 M, 11.5 mL, 2.3 mmol) and tributylamine (1.3 mL, 5.2 mmol) was added. After 20 min a solution of iodine (295 mg, 1.15 mmol) and water (0.46 mL) in pyridine (23 mL) was added. After 30 min the reaction was quenched by the addition of aqueous Na$_2$SO$_3$ (5%, 0.5 mL). The solvents were removed in vacuo. The residue was treated with NH$_4$OH (conc., 40 mL) for 4 h at room temperature and the mixture was lyophilized. The residue was dissolved in water (45 mL), and the mixture was filtered (0.2 μm). Purification by ion-exchange HPLC (Dionex BioLC DNAPac PA-100, 22×250 mm, eluent A=water, eluent B=1 M aq. NH$_4$HCO$_3$, constant A for 5 min, then gradient from 0 to 50% B in 25 min, flow rate=10 mL/min, R$_t$=12-15 min) gave 3'-OH triphosphate (180 μmol, 22%) as a colorless foam after lyophilization.

$^1$H-NMR (D$_2$O, 300 MHz): δ 7.61 (s, 1H), 4.88 (m, 1H), 4.35 (m, 1H), 4.17 (m, 1H), 4.09 (m, 1H), 3.78-3.95 (m, 5H), 3.07 (m, 1H), 2.95 (m, 1H), 1.98-2.07 (m, 2H), 1.78 (m, 1H), 1.28 (s, 3H), 1.24 (s, 9H), 1.18 (s, 3H); $^{31}$P-NMR (D$_2$O, 120 MHz): δ −6.1 (d, P); −10.1 (d, 1P); −21.6 (t, 1P).

To a 10 mM solution of 3'-OH triphosphate (5 mL, 50 mmol) was added DOWEX 50WX2. The reaction mixture was heated at 55° C. for 2 h, diluted with water (20 mL) and filtered (0.2 μm). Purification by reverse phase HPLC (Sunfire Prep C$_{18}$ column, Sum, 30×250 mm, eluent A=25 mM TEAA pH 7, eluent B=50% CH$_3$CN in A, gradient from 0 to 100% B in 30 min, flow rate=10 mL/min, R$_t$=14 min) gave compound 17 (30 μmol) as a colorless foam after lyophilization.

$^1$H-NMR (D$_2$O, 300 MHz): δ 7.68 (s, 1H), 4.95 (m, 1H), 4.38 (m, 1H), 3.64-3.98 (m, 6H), 3.48 (m, 1H), 2.81-2.89 (m, 2H), 2.13 (m, 1H), 1.86-1.96 (m, 2H), 1.65 (m, 1H); $^{31}$P-NMR (D$_2$O, 120 MHz): δ −8.3 (d, P); −10.2 (d, 1P); −21.9 (t, 1P).

BODIPY 576/589 Labeled 1-(5-amino-3,4-dihydroxypentyl)-2'-deoxy-pseudouridine-5'-triphosphate (18)

A solution of compound 17 (8 mmol) in aqueous K$_2$HPO$_4$ (0.5 M, 0.5 mL) was mixed with a solution of BODIPY 576/589-OSu (5 mg) in DMSO (0.6 mL) and acetone (0.3 mL). The mixture was incubated at RT in the dark for 2 h. The mixture was diluted with water (15 mL) and resolved by ion-exchange HPLC (Dionex BioLC DNAPac PA-100, 22×250 mm, eluent A=water, eluent B=1 M aq. $NH_4HCO_3$, C=$CH_3CN$, gradient from 80% A/20% C to 40% A/40% B/20% C in 30 min, flow rate=10 mL/min, $R_f$=16 mM), to give compound 18.

Cleavage of Scarless Linker and Elimination of Scar

The diol linker is cleavable by periodate within seconds at room temperature. The remaining aldehyde can form an imine which is activated towards base catalyzed beta-elimination under sufficiently mild conditions, with the nucleobase acting as the leaving group.

To develop the reagents for elimination of scar triphosphate-aldehyde which was obtained from the treatment of compound 17 with 10 mM $NaIO_4$ was used as model compound. A variety of conditions were explored that might eliminate the scar and the reaction was analyzed by ion-exchange HPLC (buffer A: water; buffer B: 1M $NH_4HCO_3$; gradient 0~35% B over 20 min).

|  |  | % Product | | | |
|---|---|---|---|---|---|
| Conditions | pH | 5 min | 10 min | 20 min | 30 min |
| A | 11.0 |  | 18 | 52 | 92 |
|  | 10.0 |  | 35 | 70 | 87 |
|  | 9.0 |  | 13 | 20 | 30 |
| B | 11.2 |  | 40 | 80 | 94 |
|  | 10.5 |  | 50 | 92 | 99 |
|  | 10.0 |  | 70 | 98 |  |
|  | 9.0 |  | 73 | 98 |  |
| C | 11.0 | 99 | 99 |  |  |
|  | 10.0 | 90 | 99 |  |  |
|  | 9.0 | 32 | 67 |  |  |

Conditions:
A: 100 mM glycine, 55° C.
B: 500 mM morpholine, 55° C.
C: 100 mM pyrrolidine, 55° C.

Enzymology

Thirteen DNA polymerases and reverse transcriptases performing well last time were tested again for their abilities to incorporate the triphosphate carrying a Bodipy 576/589 fluor (FIG. 6). The incubation time was extended to 30 min to see the boundaries for the enzymes to still consume all the primer s without leading to N+2 bands. The result (see next page) showed that most of the polymerases and reverse transcriptases might achieve this goal even if the incubation time was extended to 30 mM. Here only trace amount of N+2 products were seen with Deep Vent (exo-) and Bst DNA polymerases.

BODIPY 576/589 Labeled 1-(5-amino-3,4-dihydroxypentyl)-2'-deoxy-pseudouridine-5'-triphosphate Standing Start Primer-Extension Assays:

Gamma-$^{32}$P-labeled primer (2.5 pmol), cold primer (22.5 pmol) and template (30 pmol) were annealed by incubation at 95° C. for 5 min in various reaction buffer and slowly cooled to room temperature, followed by the addition of various DNA polymerase and reverse transcriptases. The extension was initiated by adding MJK's nucleoside triphosphates (MJ-008-065) (final concentration of 100 µM). After 30 min, the reaction was quenched by 10 mM EDTA in formamide loading buffer (20 µL); products were resolved by 14% PAGE.
5'-GCG TAA TAC GAC TCA CTA TGG ACG P1
CGC ATT ATG CTG AGT GAT ACC TGC AAT GTG CTT CTT CTG-5' Template AA (DNA Template)

Example 2

Synthesis of a Representative C Analog

Following a literature procedure [Wellington et al, 2009], see also [Bhattacharya et al, 1995], a mixture of $Pd(OAc)_2$ (36 mg, 0.16 mmol) and $AsPh_3$ (98 mg, 0.32 mmol) in anhydrous DMF (10 mL) is stirred at rt for 30 min. It is added to a mixture of glycal 1 (280 mg, 0.80 mmol), 5-iodoheterocycle 2 (200 mg, 0.80 mmol), and tributylamine (0.28 mL, 0.12 mmol) in DMF (10 mL).

The resulting mixture is stirred at 60° C. overnight. After cooling, the mixture is treated with acetic acid (0.2 mL) and TBAF (1M in THF, 2 mL) and stirred at rt for 1 h. Volatiles are removed by rotary evaporation under reduced pressure. The product is purified from the residue by flash chromatography (silica, gradient $CH_2Cl_2$: MeOH=15:1 to 10:1). The appropriate fraction (by tlc) is collected, evaporated and dissolved in acetic acid/acetonitrile (7 mL/7 mL). To this solution is added $NaBH(OAc)_3$ (370 mg, 1.75 mmol) at 0° C. and stirred for 2 h. Volatiles are removed by rotary evaporation under reduced pressure. The product is purified from the residue by flash chromatography (silica, gradient $CH_2Cl_2$:MeOH=7:1 to 4:1) to give a white solid (100 mg, 51%).

Example 3

Synthesis of a Representative a Analog

The 9-deazapurine skeleton is prepared by the method of Liu et al. [Liu et al, 2005], which is incorporated in its entirety herein by reference.

The heterocycle and various corresponding nucleosides for the 8-aza-9-deaza purine skeleton implementation of the adenine analog for the second architecture is well known from the natural product formycin, as are modified formycins carrying a tag on the N7 position (purine numbering). The following references are incorporated in their entirety by citation [Rosemeyer et al 1997][Muehlegger et al, 1996][Muhlegger et al, 2001][Seela et al, 1996].

Example 4

Synthesis of a Representative G Analog

The formycin analogs for guanosine nucleosides are well known, as are modified heterocycles carrying a tag on the N7 position (purine numbering). The following reference is incorporated in its entirety by citation [Sanghvi et al, 1991].

Example 5

Cleavage of Scarless Linker

The aldehyde (~3 mg) in FIG. 7, prepared by the periodate cleavage of the corresponding diol, 1 was incubated under the following conditions. The reaction was monitored by reverse HPLC($C_{18}$ column, buffer A: 25 mM TEAA, pH 7; buffer B: acetonitrile; gradient: 0-40% B over 30 minutes).
Conditions: (A-1) pH 11(0.1 M $NaHCO_3$), rt; (A-2) pH 11, 37° C.; (A-3) pH 11, 55° C.
(B-1) pH 11.8 (0.1 M CAPS), rt; (B-2) pH 11.8, 37° C.; (B-3) pH 11.8, 55° C.
(1) Condition A-1 (FIG. 8)
After 24 h incubation most starting material had disappeared.

(2) Condition A-2 (FIG. 9)
The reaction was monitored after 10 mM, 20 mM, 30 min, 1 h, and 2 h, but the reaction was not completed after 2 h incubation.
(3) Condition A-3 (FIG. 10)
Under this condition, the reaction was completed in 20 mM. From these results, the cleavage reaction can be done in pH 11 at 55° C. in less than 20 min and also in pH 11.8 at 37 or 55° C. in 1020 min.
(4) Condition B-1 (FIG. 11)
Under this condition, the reaction was faster than condition A-1, but it took more than 7 h to complete the reaction.
(5) Condition B-2 (FIG. 12)
The reaction was completed in 1020 min.
(6) Condition B-3 (FIG. 13)
The reaction was completed in 10~20 min.
With an amine as a catalyst, the following rates of cleavage were measured.

|            |      | % Product |        |        |        |
|------------|------|-----------|--------|--------|--------|
| Conditions | pH   | 5 min     | 10 min | 20 min | 30 min |
| A          | 11.0 |           |        |        | 92     |
|            | 10.0 |           | 35     | 70     | 87     |
|            | 9.0  |           | 13     | 35     | 30     |
| B          | 11.2 |           | 40     | 80     | 94     |
|            | 10.5 |           | 50     | 92     | 99     |
|            | 10.0 |           | 70     | 98     |        |
|            | 9.0  |           | 73     | 98     |        |
| C          | 11.0 | 99        | 99     |        |        |
|            | 10.0 | 90        | 99     |        |        |
|            | 9.0  | 32        | 67     |        |        |

REFERENCES

Metzker, M. L. (2005) Emerging technologies in DNA sequencing. *Genome Res.* 15, 1767-1776 Ruparel, H.; Bi, L. R.; Li, Z. M.; Bai, X. P.; Kim, D. H.; Turro, N. J.; Ju, J. Y. Design and synthesis of a 3'-O-allyl photocleavable fluorescent nucleotide as a reversible terminator for DNA sequencing by synthesis. *Proc. Natl. Acad. Sci. USA* 2005, 102, 5932-5937

Ju, J. Y.; Kim, D. H.; Bi, L. R.; Meng, Q. L.; Bai, X. P.; Li, Z. M.; Li, X. X.; Marma, M. S.; Shi, S.; Wu, J.; Edwards, J. R.; Romu, A.; Turro, N. J. Four-color DNA sequencing by synthesis using cleavable fluorescent nucleotide reversible terminators. *Proc. Natl. Acad. Sci. USA* 2006, 103, 19635-19640

Guo, J.; Xu, N.; Li, Z. M.; Zhang, S. L.; Wu, J.; Kim, D. H.; Marma, M. S.; Meng, Q. L.; Cao, H. Y.; Li, X. X.; Shi, S. D.; Yu, L.; Kalachikov, S.; Russo, J. J.; Turro, N. J.; Ju, J. Y. Four-color DNA sequencing with 3'-O-modified nucleotide reversible terminators and chemically cleavable fluorescent dideoxynucleotides. *Proc. Natl. Acad. Sci. USA* 2008, 105, 9145-9150

Benner, S. A. Method for sequencing DNA and RNA by synthesis. 2009, U.S. Pat. No. 7,544,794

Tasara, T.; Angerer, B.; Damond, M.; Winter, H.; Doerhoefer, S.; Huebscher, U.; Amacker, M. Incorporation of reporter molecule-labeled nucleotides by DNA polymerases. II. High-density labeling of natural DNA. *Nucl. Acids Res.* 2003, 31, 2636-2646

Wu, W.; Stupi, B. P.; Litosh, V. A.; Mansouri, D.; Farley, D.; Morris, S.; Metzker, S.; Metzker, M. L. Termination of DNA synthesis by N6-alkylated, not 3'-O-alkylated, photocleavable 2'-deoxyadenosine triphosphates. *Nucleic Acids Res.* 2007, 35, 6339-6449. *Nucleic Acids Res.* 2007, 35, 6339-6449

Siddiqi, S. (2008) Nucleic Acid Analogs, WO 2008/144544

Luyten, I., Thibaudeau C., Chattopadhyaya, J. (1997) The determination of the ionization constants of C-nucleosides. *Tetrahedron* 53, 6903-6906

Ludwig, J.; Eckstein, F. Rapid and efficient synthesis of nucleoside 5'-O-(1-thiotriphosphates), 5'-triphosphates and 2',3'-cyclophosphorothioates using 2-chloro-4H-1,3, 2-benzodioxaphosphorin-4-one. *J. Org. Chem.* 1989, 54, 631-635

Wellington, K. W., Ooi, H. C., Benner, S. A. (2009) Convenient synthesis of N,N'-dibenzyl-2,4-diaminopyrimidine-2'-deoxyribonucleoside and 1-methyl-2'-deoxypseudoisocytidine. *Nucleosides Nucleotides & Nucleic Acids* 28, 275-291

Bhattacharya, B. K.; Devivar, R. V.; Revankar, G. R. (1995) A practical synthesis of N1-methyl-2'-deoxy-☐-uridine(☐-thymidine) and its incorporation into G-rich triple helix forming oligonucleotides. *Nucleosides & Nucleotides* 14, 1269-1287

Liu, M-C., Luo, M-Z., Mozdziesz, D. E., Sartorelli, A. C. (2005) Synthesis and biological evaluation of 2- and 7-substituted 9-deazaadenosine analogs. *Nucleosides, Nucleotides & Nucleic Acids* 24, 45-62

Rosemeyer, H.; Zulauf, M.; Ramzaeva, N.; Becher, G.; Feiling, E.; Muhlegger, K.; Munster, I.; Lohmann, A.; Seela, S. (1997) Stereoelectronic effects of modified purines on the sugar conformation of nucleosides and fluorescence properties. *Nucleosides & Nucleotides* 16, 821-828.

Muehlegger, K.; Eltz, H.; Seela, F. (1996) Preparation of C-nucleoside derivatives for use in DNA sequencing, in situ hybridization, detection and marking of nucleic acids, and oligonucleotide chemical synthesis. Ger. Offen., 10 pp. CODEN: GWXXBX DE 19509038 A1 19960919 CAN 125:276441 AN 1996:628561

Muhlegger, K.; Von der Eltz, H.; Seela, F.; Rosemeyer, H. (2001) C-nucleoside derivatives and their use in the detection of nucleic acids. U.S. Pat. No. 6,174,998.

Seela, F.; Chen, Y.; Melenewski, A.; Rosemeyer, H.; Wei, C. (1996) Synthesis and application of novel nucleoside phosphonates and phosphoramidites modified at the base moiety. *Acta Biochimica Polonica* 43, 45-52.

Sanghvi, Y. S.; Larson, S. B.; Smee, D. F.; Revankar, G. R.; Robins, R. K. (1991). In vivo antiviral activity of 5-amino-1-methyl-3-☐-D-ribofuranosylpyrazolo[4,3-d]pyrimidin-7(6H)-one and related guanosine analogs prepared from formycin. *Nucleosides & Nucleotides* 10, 1417-1427.

What is claimed is:

1. A compound having the structure

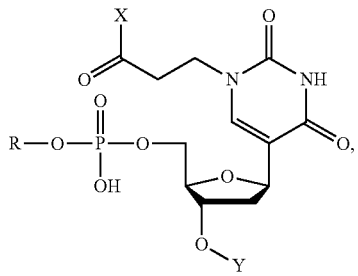

wherein X is selected from the group consisting of H and alkyl, wherein Y is selected from the group consisting of H and an oligonucleotide, and wherein R is selected from the group consisting of H and an oligonucleotide.

2. The compound of claim 1 having the structure

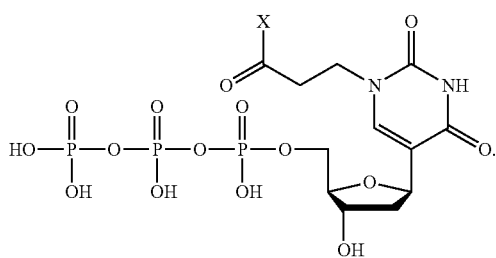

* * * * *